United States Patent [19]

Pomares et al.

[11] Patent Number: 5,216,789
[45] Date of Patent: Jun. 8, 1993

[54] METHOD AND APPARATUS FOR STERILIZATION AND/OR EMBALMENT OF CORPSES AND SPECIMENS

[75] Inventors: Raul J. Pomares, Livermore; Fernando Velez, Capitola, both of Calif.

[73] Assignee: Technology Application Services, San Jose, Calif.

[21] Appl. No.: 701,531

[22] Filed: May 16, 1991

[51] Int. Cl.⁵ ............................................. A01N 1/00
[52] U.S. Cl. .................................. 27/22.1; 27/23.1
[58] Field of Search ..................... 27/21, 22.1, 23; 250/492.1; 378/68, 117, 194, 197

[56] References Cited

U.S. PATENT DOCUMENTS

| | | |
|---|---|---|
| 746,284 | 12/1903 | Carleton . |
| 2,640,159 | 5/1953 | Gerneth . |
| 3,435,494 | 4/1969 | Bernard . |
| 3,494,723 | 2/1970 | Gray . |
| 3,494,724 | 2/1970 | Gray . |
| 3,638,709 | 2/1972 | Brown, Jr. et al. . |
| 4,121,107 | 10/1978 | Bachmann . |
| 4,351,091 | 9/1982 | Goodkin . |
| 4,666,478 | 5/1987 | Boissinot et al. . |
| 4,877,964 | 10/1989 | Tanaka et al. . |
| 4,879,789 | 11/1989 | Bak . |

OTHER PUBLICATIONS

National FS Journal, vol. 74, No. 7, Jul., 1960 "Preservation of Human Remains by Radiation".

Primary Examiner—Richard E. Chilcot, Jr.
Attorney, Agent, or Firm—Townsend and Townsend Khourie and Crew

[57] ABSTRACT

A preservation system (2) for cadavers and the like. A chamber (6) is defined by walls (4) which are of sufficient thickness to block gamma irradiation from a gamma source (20) therein. The gamma source is placed in a conveyor system (32) and moved around a cadaver in the chamber, killing microorganisms therein, and returned to a storage area (14). A bagging system (35) seals the cadaver after irradiation.

30 Claims, 5 Drawing Sheets

METHOD AND APPARATUS FOR STERILIZATION AND/OR EMBALMENT OF CORPSES AND SPECIMENS

BACKGROUND OF THE INVENTION

The present invention relates to the field of preservation of biological specimens. More specifically, in one embodiment the invention provides a method and apparatus for sterilization and/or embalment of corpses and other specimens.

A variety of techniques are available for preservation of biological materials such as corpses. The most prevalent among such techniques is embalming. In an embalming process, natural fluids are removed from the body and replaced with a suitable preservative such as formaldehyde. This process has a number of attributes which have lead to its being widely adopted for corpse preservation.

The embalming process suffers from a number of limitations however. For example, often it is desirable to preserve a corpse for later investigation such as, for example, by medical students and the like. However, the embalming process results in substantial damage to tissues, particularly at a microscopic level. This arises due to physical damage from excess pressure, incompatibility of the preservation fluid with microscopic features of the body, damage to capillaries, interaction of preservation fluid with tissue, and the like. Furthermore, the process generally must be performed by those with sufficient skill in the process, requires a substantial amount of time to perform, and requires specialized facilities, which are often not portable. Consequently, during major disasters such as earthquakes, floods, and the like, bodies often accumulate and contribute to the spread of disease, among other problems. Further, the process does not preserve the corpse for a sufficiently long period of time often requiring additional measures such as refrigeration. Still further, it becomes necessary for involved personnel to be exposed excessively to potentially harmful organisms in the body during the embalming process.

Alternative methods and devices for corpse preservation have been proposed. For example, it has been proposed to irradiate cadavers using x-rays or gamma rays after a heat treatment. An example of such a system is discussed in U.S. Pat. No. 4,351,091 in which a body is placed in a plastic box and the box is heated, then irradiated.

Such systems suffer from a variety of limitations. For example, after the body is irradiated, the container in which the cadaver is contained must remain sealed, sealing thereof being an important part of the process, and the cadaver will immediately begin decomposition after removal from the case. Further, the materials utilized for the case will often degrade when radiation of sufficient energy is utilized, particularly when radiation is applied from a location outside the case.

From the above it is seen that an improved method and apparatus for the preservation of cadavers and the like is desired.

SUMMARY OF THE INVENTION

An improved method and apparatus for the preservation of cadavers and other animal specimens is provided by virtue of the present invention. The invention provides a container in which a human cadaver or other animal specimen is inserted. The specimen is irradiated with, preferably, gamma rays. The gamma rays kill bacterial and other micro-organisms which cause undesirable decomposition of the cadaver. According to preferred embodiments, the device is mobile (mounted on casters, for example) and is substantially self-contained, providing the ability to transport the device to, for example, a disaster sight.

Preferably, the device includes a main chamber into which the cadaver is inserted. The main chamber is enclosed by a radiation shielding structure. The gamma ray source is further contained within the preferably cylindrical radiation shielding device and emerges along a conveyor system to irradiate the cadaver, returning to the radiation shielding device after irradiation is complete.

After completion of the irradiation step and subsequent return of the radiation source to the radiation shielding device, the cadaver is bagged as it is withdrawn while contained within the main chamber, without breaching the main chamber environment. A vacuum pump is provided for removal of air during bagging. Once the cadaver is placed in the bag, vacuum is applied and the bag is sealed. The bag is formed of a plastic material and is sealed using radio frequency welding or similar methods. Therefore, the cadaver will be preserved for long periods of time, even after removal from the main chamber.

Accordingly, in one embodiment the invention includes a radiation source, the radiation source adapted to kill microorganisms in an adjacent cadaver; means for holding a mammalian cadaver; and chamber walls defining a chamber therein into which the means for holding is inserted, the chamber adapted to receive the radiation source, the chamber shielding walls blocking to allowable levels the radiation from the radiation source.

A further understanding of the nature and advantages of the inventions herein may be realized by reference to the remaining portions of the specification and the attached drawings.

DESCRIPTION OF THE PREFERRED EMBODIMENTS

Figure 1:
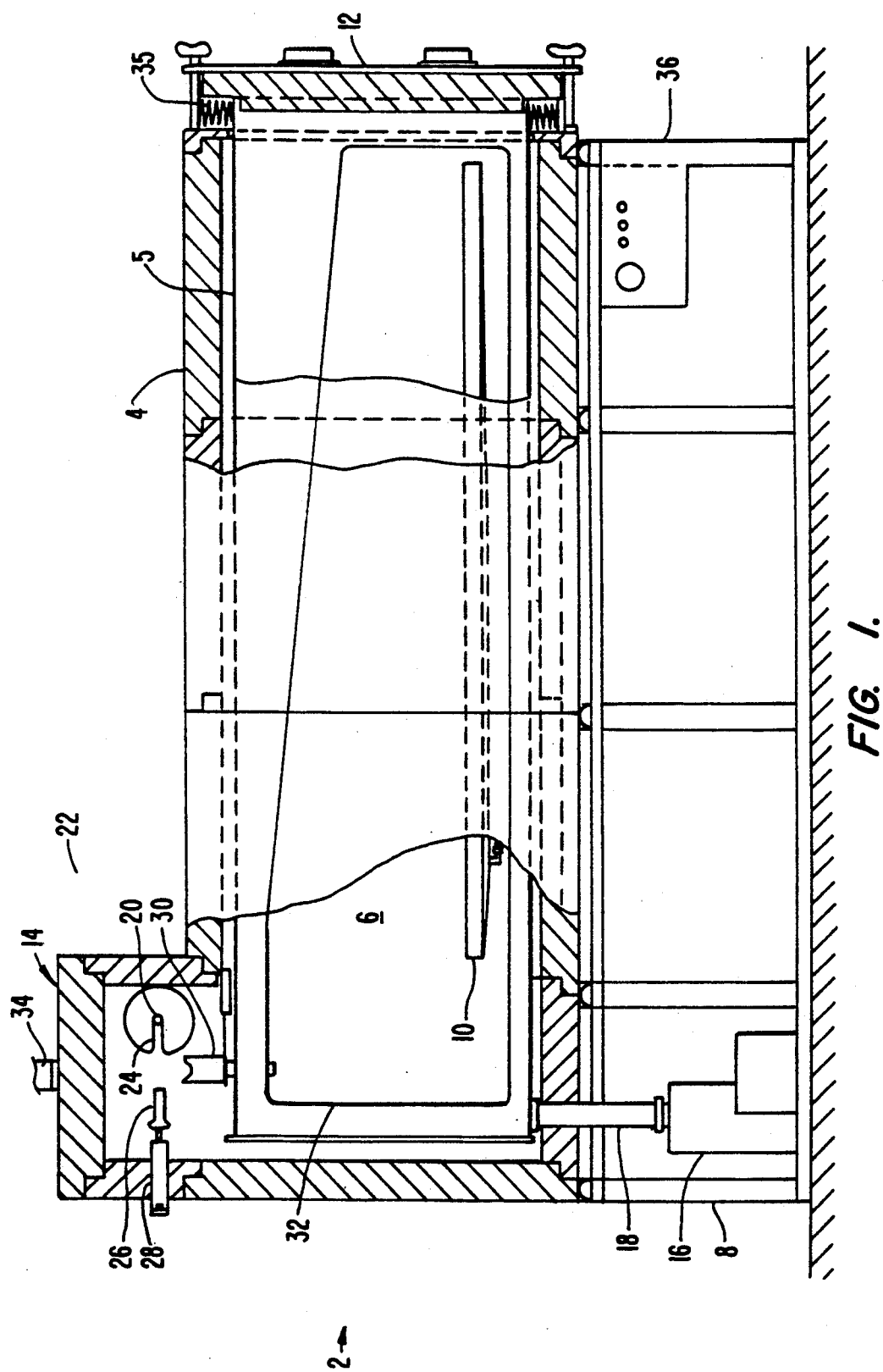
FIG. 1 is a cross-section of one embodiment of the invention.

FIG. 1 is a side view of a first embodiment of a corpus irradiator 2, partially cut away. The irradiator includes a shielding block or blocks 4 which are arranged to enclose the generally rectangular main chamber 6. The shielding blocks are formed from a material which will substantially attenuate gamma ray radiation from passing out of the chamber. The shielding blocks are also formed from a material which mechanical characteristics will not change after prolonged and repeated exposure to a radiation source therein (such as the preferred gamma ray radiation source). In preferred embodiments, the shielding blocks are formed from lead encased by carbon steel materials, although other materials such as tungsten, depleted uranium, or other high density materials will be used in some embodiments. The shielding blocks are of sufficient thickness to prevent passage of substantial amounts of radiation and preferably have a thickness of between about 2 and 6 inches, with most preferred thicknesses of between about 4 and 6 inches (based on lead and carbon steel walls). Preferably, the shielding will attenuate to allowable levels mandated by government regulatory agencies such as those mandated by 10 CFR 20. Shielding is provided for the radiation source for storage and additional shielding during operations in which the door is open. The irradiator is optionally mounted on a base structure 8 which houses the irradiator support equipment, vacuum and filter units.

The dimensions of the main chamber should be large enough to contain a cadaver. The internal length of the main chamber should be greater than about 8 feet, and preferably greater than about 10 feet. The width and height of the chamber should be greater than about 28 inches, and preferably greater than about 36 inches.

Inside the main chamber a sliding tray 10 is mounted. The tray is preferably sized to conveniently hold a human or animal cadaver and is preferably slidable from a first end of the main chamber on which a door 12 is mounted to a second end of the main chamber in which a radiation source assembly 14 is mounted. As used herein the term cadaver is intended to include bodies or substantial portions thereof which are to be preserved for burial, medical investigation, or the like. Optionally, the tray is slidable to a position outside of the door such that a cadaver or specimen will be more easily placed thereon. The tray is slidably mounted within the chamber for ease of loading and unloading of the specimen. The slidable tray is preferably made from a material and of a sufficient thickness which will allow the passage of radiation such as gamma ray radiation. Such materials include stainless steel having a thickness of about 0.06 inches. In preferred embodiments the tray is elevated above the floor of the main chamber such that the source may pass thereunder and continue on a path around the entire length of the tray, both above and below the tray. Accordingly, the tray(s) is preferably slidably mounted to the sidewalls of the main chamber about 6 to 8 inches above the bottom chamber floor. Compensation for any blockage of the radiation by the tray is achieved by placing the source in closer proximity to the body when under the tray.

Although not shown in the figure, it will be apparent that multiple stacked trays and, accordingly a more complex source path, may be provided according to some embodiments for processing of multiple specimens. In such embodiments, the source will preferably trace a path between each tray.

A vacuum and filter system 16 is connected to the main chamber via an air passage or tube 18. The vacuum and filter assembly has two primary functions. First, to evacuate the main chamber after the irradiation operations, such that it becomes possible to ensure that undesirable microorganisms do not pass through any small leaks in the main chamber, and such that a bag (discussed below) will seal tightly around the specimen. Furthermore, the filter assembly processes any air which is drawn through the system to ensure that undesirable particles are removed therefrom. In preferred embodiments, the vacuum assembly is designed to maintain a vacuum of about 26 inches Hg, and preferably about 20 inches Hg during normal operation. Suitable filter assemblies include a filter housing and a high efficiency filter for retention of 0.3 microns, or greater particles. The vacuum is preferably maintained at a level that will not boil water. Importantly, the vacuum substantially eliminates oxygen so as to reduce or eliminate oxidation processes on the specimen.

Inside or adjacent the main chamber, radiation source assembly 14 is provided. Inside the radiation source assembly shown in FIG. 1 a radiation source 20 is normally retained within a source shield 22. According to preferred embodiments the source is a cylindrical bar or rod of, for example, cesium (137) or cobalt pellets in a stainless steel tube inserted in another stainless steel tube to meet special form standards. Such sources are made by General Electric, Westinghouse, or Hanford National Laboratory. The source is of a type and energy such that microorganisms and bacteria in a cadaver will be killed when the source is placed a short distance from the cadaver (i.e., less than about 2 feet) for a reasonable length of time. Typically 20,000 curies of cobalt (1.3 rad/curie for cobalt) are used according to preferred embodiments, although a wide range of easily determined source strengths may readily be used depending on the acceptable time period for irradiation, the expected specimen sizes, and the like. The source will be of sufficient strength to kill microorganisms in an adjacent cadaver. For example, in some embodiments the source strength may range from 0.1 times to 100 times the above values. It will be recognized that while the invention is illustrated herein with regard to the use of gamma rays, the invention is not so limited.

In the embodiment shown in FIG. 1 the source is a bar or rod having a diameter of between about 0.375 and 3.0 inches, with a preferred range of between about 0.4 and 2.5 inches. As shown, the rod preferably has a length such that it spans substantially all of the inside width of the chamber such as about 85% or more of the chamber, and at least having a width of the tray.

The source 20 is stored in source shield 22 when the device is not in use or when the door is opened for loading and unloading operations. The source shield 22 in the embodiment shown in FIG. 1 is a cylindrically shaped bar of high density material having a diameter of between about 6 and 8 inches. Preferably, tungsten is utilized due to the desirable small size of the shield, but alternatively, depleted uranium or the like is utilized. On one side of the source shield 22 a slot 24 is provided through which the rod 20 is withdrawn and stored. A removable wedge 26 is insertable into the slot 24 by way of a source wedge actuator 28 which may be, for example, a slidable rod extending out of the device, or a motorized and automated device for removal of the wedge. The source shield may be used as an inner container during transportation of the source from the source manufacturer and the irradiation facility.

Between the source assembly 14 and the main chamber 6 a source chute 30 is provided for passage of the source 20. Extending from the source shield through the source chute and into the main chamber a source conveyor 32 is provided. According to preferred embodiments, the source conveyor is adapted to move the source from the source assembly 14, optionally into or from the main chamber, and along a substantial portion of the length of the main chamber such as more than 85% of the length of the chamber, preferably more than 90% of the length of the chamber, and more preferably along the entire length of the chamber. In most preferred embodiments, the source conveyor extends fully around the tray 10 such that the radiation source is moved completely around the cadaver. This motion allows for ensured complete sterilization of the cadaver while using a source which has a power level which is safe for operation. In preferred embodiments the path of the source conveyor maintains the source at a distance from the cadaver such that the radiation exposure is as uniform as possible throughout the trajectory around the specimen. Therefore, the source is closer to the cadaver when underneath the tray and farther away above the cadaver.

In some embodiments the source is placed into the conveyor system by way of a source placement actuator 34. The source placement actuator is adapted to remove the source from the source assembly and place it on the conveyor. As shown in FIG. 1, the wedge 26 is lowered to a position such that the source 20 is placed in the conveyor system. After completing a pass through the chamber, the source is placed on the wedge, and the wedge is raised back into the shield.

At one end of the irradiator, preferably at the door end of the irradiator, a bagging assembly 35 is provided. The bagging assembly contains a suitable airtight bag such as a plastic bag made of polyvinyl chloride or polyethylene, which is bundled into a recess of the irradiator door. The bag must be placed in a shielded location because gamma radiation of the intensity used herein will tend to have an adverse effect on most plastics. The bagging assembly is designed such that after irradiation of the cadaver but before removal, the cadaver is brought into the bag and a vacuum is applied. Accordingly, after sterilization of the cadaver, there is little or no exposure to microorganisms which could again start the decay process.

All operations are conducted under the direction of control assembly 36. The control assembly controls such functions as vacuum, duration, speed, exposure level or rate, bagging process, drive controls, lens or wedge control (shield), filtering system, source position, etc.

In operation, the source is normally contained within the source shield and the wedge is inserted therein. The tray is slid from the main chamber and a cadaver is placed thereon. The tray is slid into the main chamber and the door is shut. The wedge is removed from the wedge actuator and the source placement actuator is used to place the source in the conveyor. After placement of the source in the conveyor, the source is moved along a path which circumnavigates the entire length of the cadaver as shown by the conveyor path 32. Preferably, the source is moved at a speed proportional to the source strength and the size of the cadaver for adequate exposure. The source is then placed back in the source shield, and the wedge is replaced. The cadaver is then brought into the bag and vacuum is applied. The bag is sealed using a conventional radio frequency welder in the preferred embodiment. Preferably, all operations are conducted at about ambient temperature so as to prevent accelerated enzymatic decomposition of the cadaver.

NRC standards require blocking as much radiation as possible. See 10 CFR 20, Standards for Protection Against Radiation (or equivalent foreign/state rules). It is expected that the system will be able to attenuate radiation on the outside of a room wall to <1 R/hour, preferably <100 mR/hour, more preferably <20 mR/hour, and most preferably <5 mR/hour. The room may also be shielded.

Figure 2:
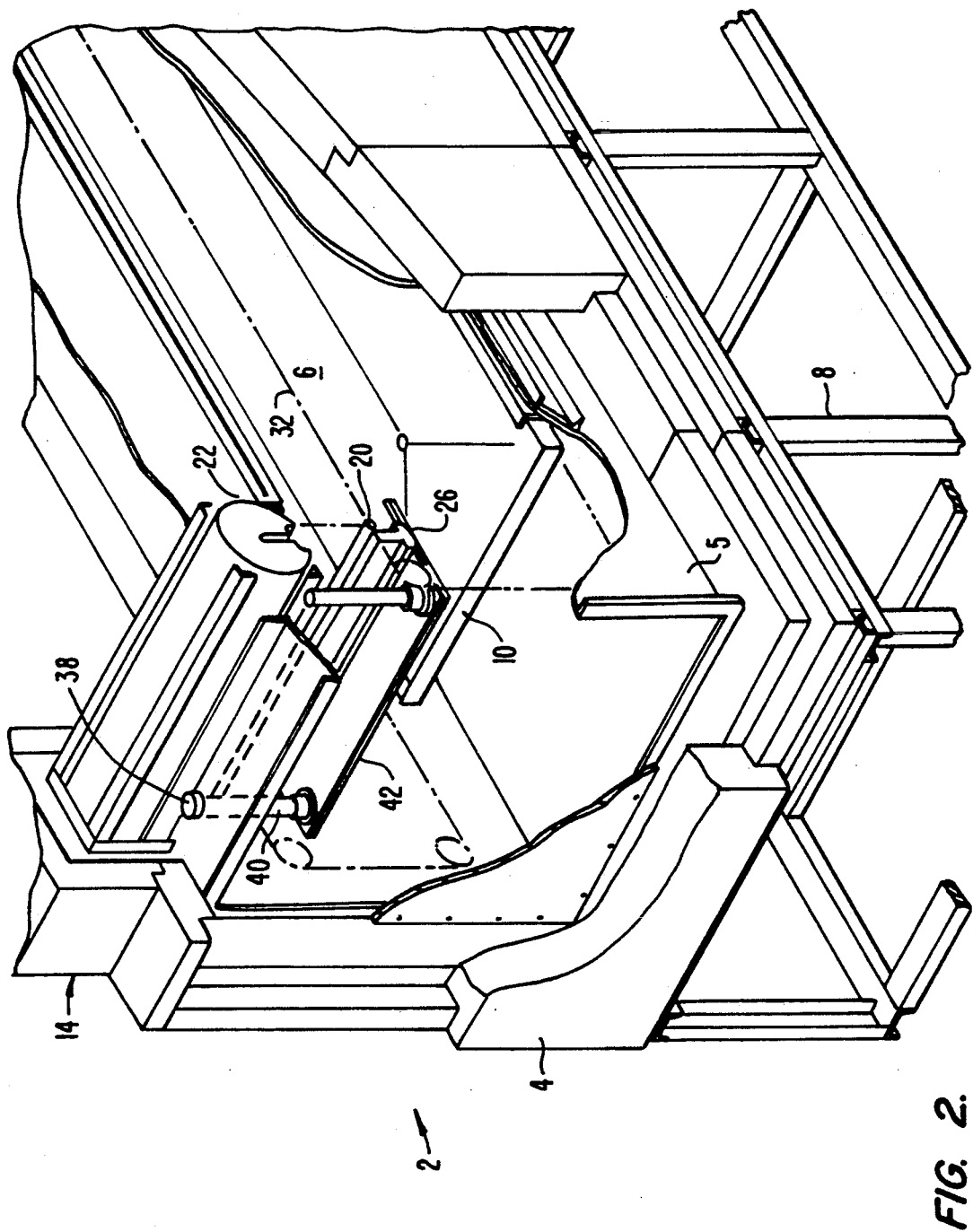
FIG. 2 is an isometric view of the invention, partially cut away to reveal important components of the source section of the device according to a second embodiment of the invention.

FIG. 2 illustrates an alternative preferred embodiment of the source assembly end of the irradiator in greater detail in isometric view. According to this embodiment of the invention, the functions of the wedge actuator 28 and the source placement actuator are combined. In particular, the wedge actuator/source placement actuator includes a rod or rods 40 extending through the wall of the device (or automatically driven via stepping motor or the like). Attached to the rods, a plate 42 is provided, onto which the wedge 26 is placed, the wedge having an upper surface for holding the source 20. In this case, the slot in the source shield 22 is downwardly facing and as the plate 42 is moved downwards with the rods 40, the source is lowered into the conveyor 32. When the source is returned to its starting location by the conveyor, the plate is raised with the rods, directing the wedge and the source back into the source shield.

Figure 3:
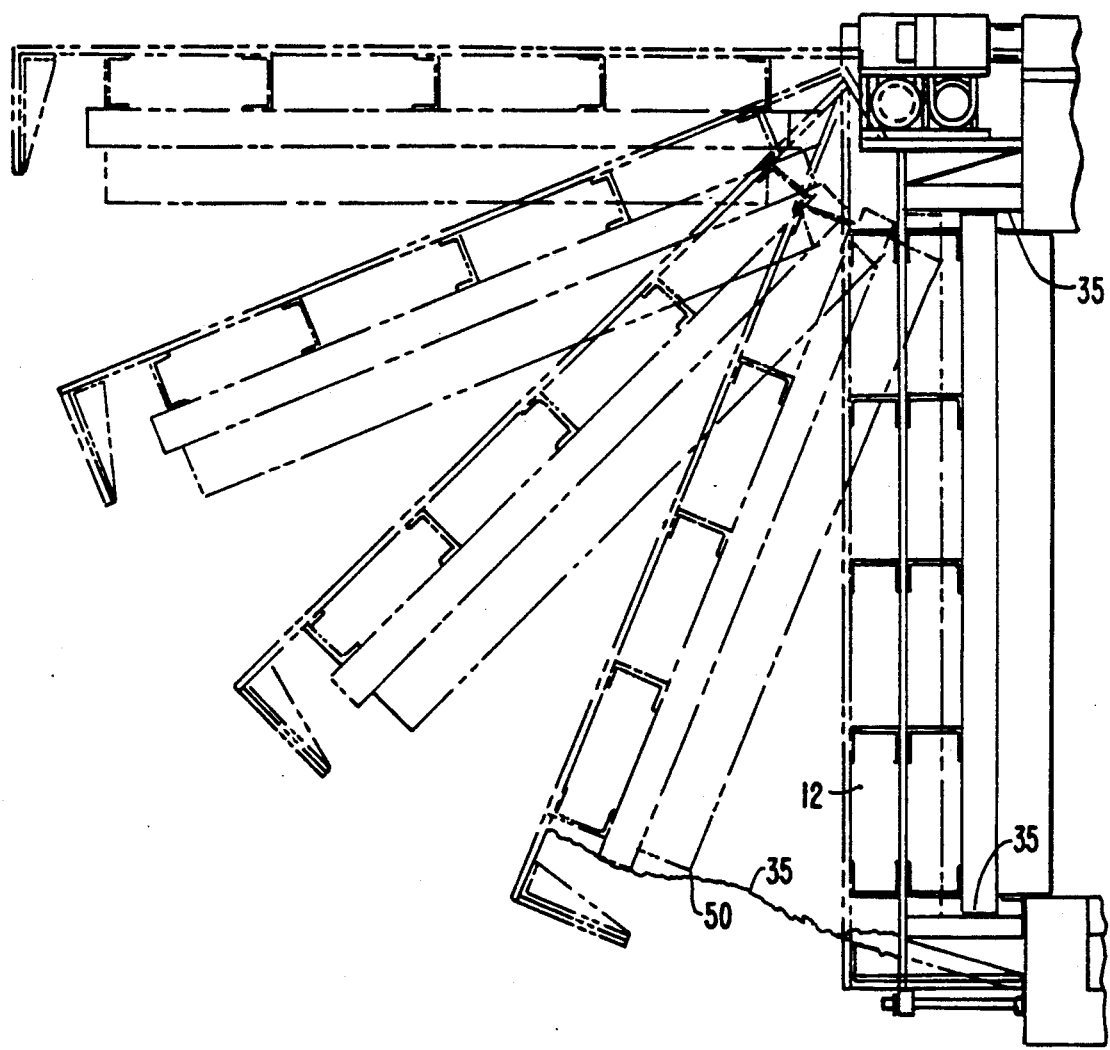
FIG. 3 is an illustration of the bagging device and method.

FIG. 3 illustrates the bagging assembly in greater detail. As shown in FIG. 3, the bag 35 is carried around the perimeter of the chamber near the 12. The door is closed for irradiation operations. When the irradiation is completed, the vacuum is applied, and the door is opened, as shown in phantom in FIG. 3. The bag, which is opened at both ends and previously packed around the outer perimeter of the main chamber, is drawn out with the door as it is opened in the manner of an accordion. Vacuum is simultaneously applied, providing a tight seal to the cadaver. The door-end of the bag is then sealed and cut using conventional radio frequency welding equipment. The tray is then slid out of the unit, and the bag covers the rest of the cadaver as it is removed. After the entire length of the cadaver is removed, the other end of the bag is sealed, also using radio frequency welding equipment.

Figure 4:
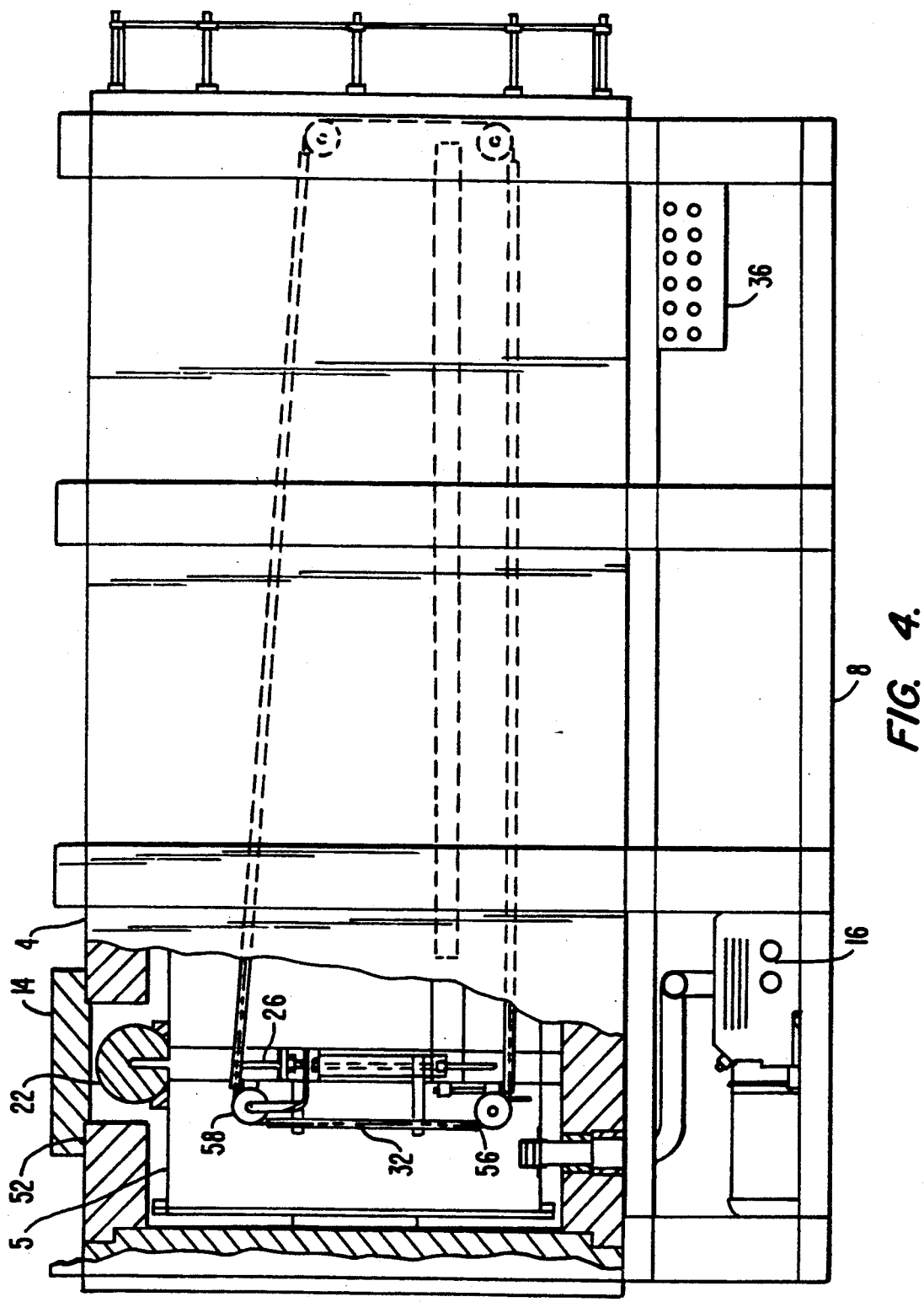
FIG. 4 illustrates another embodiment of the invention with greater details of the source conveyor.

FIG. 4, in which common reference numerals refer to common items, illustrates an alternative preferred embodiment of the system, including greater details of the conveyor system. In the embodiment shown in FIG. 4, the housing for the source shield does not extend from the top of the chamber 4 a substantial distance. Instead the top of the source shield 22 is placed at approximately the same level as the top of the main chamber. The housing 14 then consists only of a block which is used to cover an opening in the chamber, through which the device is serviced, and the like. As shown in FIG. 4, the housing block 14 is provided with substantial overlap regions 52 over the main chamber walls to ensure blockage of radiation.

The conveyor system 32 as shown in FIG. 4 includes a cable 56 which is routed around a system of four or more pulleys 58 on each side of the main chamber. As the source (not shown) is lowered by the wedge 26, it engages the cable and is thereafter transported around the inside of the chamber by the cable. A manual crank may optionally be provided to allow for system or power failures. The source is placed on the cable for traversal of the main chamber, and then returned to the source shield.

Figure 5:
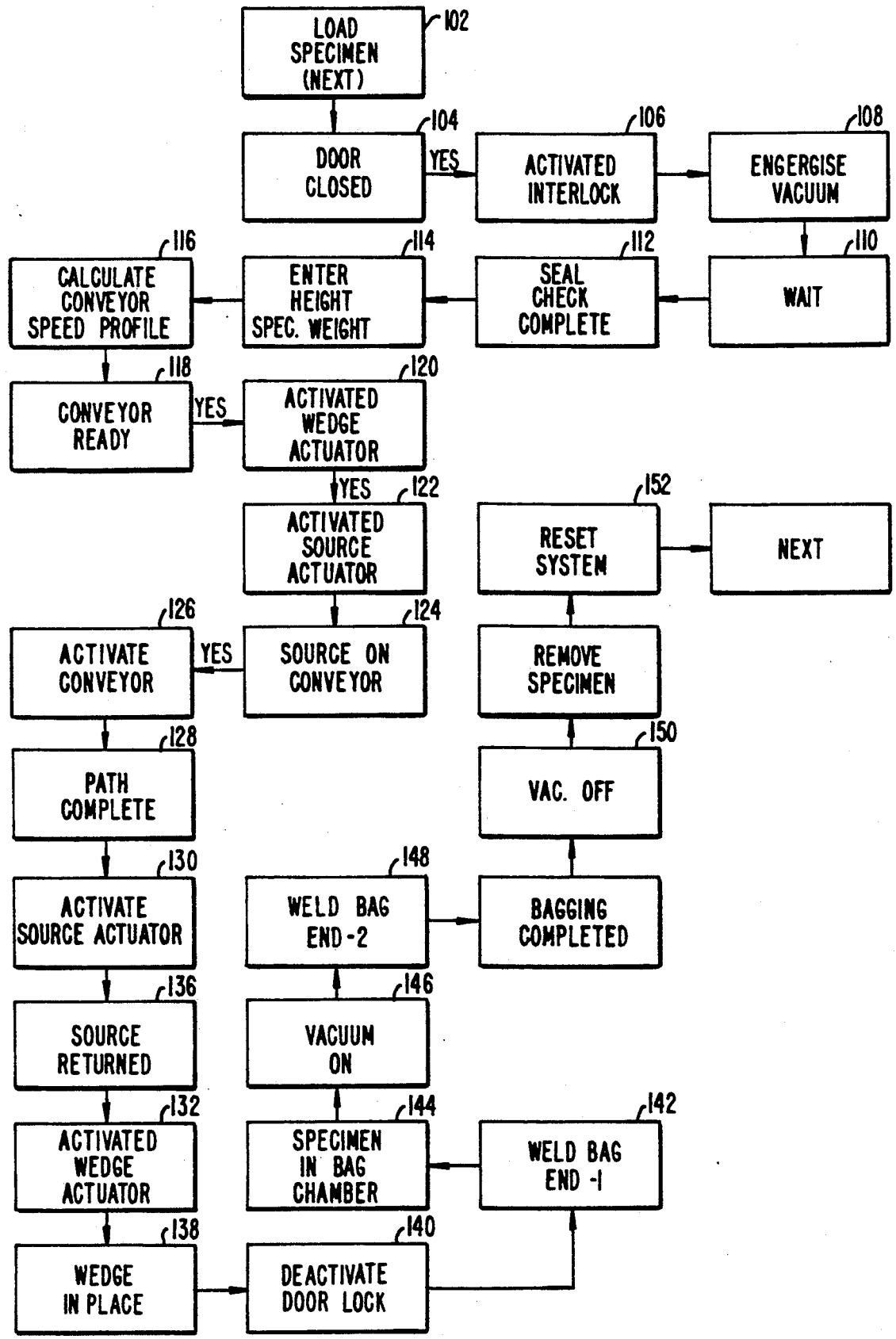
FIG. 5 is a flow chart illustrating operation of the control system.

FIG. 5 is a flow chart illustrating operation of the control system for the system, the control system using an appropriately programmed microprocessor of the type well known to those of skill in the art according to preferred embodiments. Initially, the specimen is loaded into the chamber at step 102. The system checks to determine if the door is closed at step 104 and, when the door is closed the system activates an interlock system at step 106 to prevent entry into the chamber until after completion of the processing. At step 108 (or, in alternative embodiments, later in the process) the vacuum is energized and at step 110 the system waits for a preset time for the vacuum to be established. At step 112 the system performs a seal check by, for example, monitoring the pressure in the chamber over a period of time.

At step 114 the system accepts input for the specimen height and weight and at step 116 calculates a conveyor profile (i.e., the speed at which the source is moved as a function of location in the chamber) which is dependent not only upon the height and weight of the specimen, but also the source strength and other parameters. At step 118 the system ensures that the conveyor is ready and at step 120 the wedge is activated for removal of the gamma source.

At step 122 the system activates the source actuator, if any, and at step 124 checks to determine if the source is on the conveyor. When the source is detected on the conveyor, the conveyor is actuated at step 126, and at step 128 the system waits until a detection is received that the path is complete. The source and wedge actuators are then activated at steps 130 and 132, respectively, and checks are performed at steps 136 and 138 to ensure that the source/wedge are properly returned. At step 140 the door lock is deactivated. The user then opens the door and welds the bag at step 142. At step 144 the specimen is removed by sliding the tray from the chamber and at step 146 the vacuum is energized, if this was not already done. The other bag end is then welded by the user at step 148 and at step 150 the vacuum is turned off. The system is then reset at step 152 after removal of the specimen.

The above description is illustrative and not restrictive. Many variations of the invention will become apparent to those of skill in the art upon review of this disclosure. Merely by way of example, the irradiator could use other sources of radiation, or could be used with mammalian specimens or portions thereof other than humans. The scope of the invention should, therefore, be determined not with reference to the above description, but instead should be determined with reference to the appended claims along with their full scope of equivalents.

What is claimed is:

1. A cadaver irradiation assembly for preservation of mammalian cadavers comprising:
   a) chamber walls defining a chamber therein;
   b) means for holding a mammalian cadaver in said chamber; and
   c) a radiation source in said chamber, said chamber walls attenuating radiation from said radiation source, said radiation source having sufficient strength to kill microorganisms in a cadaver on said means for holding.

2. The cadaver irradiation assembly as recited in claim 1 wherein said radiation source is a gamma ray radiation source.

3. The cadaver irradiation assembly as recited in claim 2 wherein said chamber walls comprise materials selected from the group consisting of tungsten, depleted uranium, and lead.

4. The cadaver irradiation assembly as recited in claim 3 wherein said walls have a thickness of between about 4 and 6 inches.

5. The cadaver irradiation assembly as recited in claim 1 further comprising a slidable tray therein, said tray slidably removable from said chamber for placement of a cadaver.

6. The cadaver irradiation assembly as recited in claim 5 wherein said tray is slidably mounted in said chamber so as to form a space between said tray and a floor of said chamber.

7. The cadaver irradiation assembly as recited in claim 6 wherein said tray permits transmission of radiation from said source into an adjacent cadaver on said tray.

8. The cadaver irradiation assembly as recited in claim 1 further comprising a vacuum pump connected to said chamber, said vacuum pump adapted to maintain a vacuum greater than about 20 inches of mercury in said main chamber during operation of said assembly.

9. The cadaver irradiation assembly as recited in claim 8 further comprising an air filter attached to said vacuum pump, said air filter adapted for removal of greater than about 0.3 micron particles.

10. The cadaver irradiation assembly as recited in claim 1 further comprising a radiation source shield in said chamber, said radiation source shield having an opening therein, said opening sealable for preventing emanation of radiation into said chamber.

11. The cadaver irradiation assembly as recited in claim 10 wherein said radiation source is a cylindrical radiation source and said radiation source shield is a cylindrical shield having a removable wedge for sealing said opening, said cylindrical radiation source insertable into said opening.

12. The cadaver irradiation assembly as recited in claim 1 further comprising means for moving said source within said chamber.

13. The cadaver irradiation assembly as recited in claim 12 wherein said means for moving is a conveyor.

14. The cadaver irradiation assembly as recited in claim 12 wherein said means for moving is adapted to move said source along at least 50% of a length of said chamber.

15. The cadaver irradiation assembly as recited in claim 12 wherein said means for moving is adapted to move said source along at least 90% of a length of said chamber.

16. The cadaver irradiation assembly as recited in claim 12 further comprising a tray for holding a cadaver and wherein said means for moving is adapted to move said source under said tray.

17. The cadaver irradiation assembly as recited in claim 16 wherein said means for moving is adapted to move said source in a complete loop around said tray.

18. The cadaver irradiation assembly as recited in claim 17 wherein said source is a cylindrical rod having a width of substantially the entire width of said chamber.

19. The cadaver irradiation assembly as recited in claim 1 further comprising means for placing a cadaver in a substantially airtight bag after irradiation thereof.

20. The cadaver irradiation assembly as recited in claim 19 wherein said means for placing comprises a bag attached to a door of said chamber, said bag attached to said door upon opening of said door after irradiation of a specimen, said bag shielded from irradiation when said door is closed.

21. The cadaver irradiation assembly as recited in claim 11 wherein said wedge is movable from a first position in said slot to a second position lower from said first position, said source moved into a conveyor system when said wedge is in said second position, said conveyor comprising at least one cable system oriented in a loop around said main chamber.

22. A cadaver irradiation system for preservation of cadavers comprising:
   a) an enclosure substantially impermeable to gamma radiation, said enclosure defining a substantially rectangular chamber;
   b) a tray for holding a cadaver above a floor of said chamber;
   c) a gamma radiation source movable into said chamber, said gamma radiation source comprising a rod, said rod extending substantially across a width of said chamber;
   d) a conveyor system for transporting said radiation source around said tray;
   e) a source shield for storage of said radiation source, said source shield substantially preventing entry of gamma radiation into said chamber when said source is in said source shield;
   f) means for placing a cadaver in a substantially airtight bag after irradiation thereof.

23. A method of preserving a mammalian cadaver comprising the steps of:
   a) inserting said mammalian cadaver into a chamber, said chamber having walls for attenuation of radiation from a radiation source therein;
   b) closing said chamber;
   c) exposing said cadaver to radiation from said radiation source in said chamber, said radiation source having sufficient strength to kill microorganisms in said cadaver;
   d) placing said radiation source in a radiation source shield in said chamber; and
   e) opening said chamber for removal of said cadaver.

24. The method as recited in claim 23 wherein said step of exposing said cadaver to radiation is a step of exposing said cadaver to a gamma ray source.

25. The method as recited in claim 24 wherein said chamber walls attenuate said radiation to less than 20 mR/hour at a wall of a room in which said chamber is contained.

26. The method as recited in claim 23 wherein said step of exposing said cadaver to radiation comprises the steps of:
   a) removing said radiation source from said radiation source shield; and
   b) moving said radiation source into proximity of said cadaver.

27. The method as recited in claim 26 wherein said step of moving said radiation source is a step of moving said source in a complete path around said cadaver.

28. The method as recited in claim 23 further comprising the step of applying a vacuum to said chamber.

29. The method as recited in claim 23 further comprising the step of placing said cadaver in an airtight container after said step of exposing.

30. The method as recited in claim 29 wherein said step of placing said cadaver in an airtight container comprises the steps of:
   a) opening a door on said chamber, a plastic bag attached to said door;
   b) sealing a first end of said bag;
   c) sliding said cadaver substantially from said chamber; and
   d) sealing a second end of said bag.

* * * * *